US009606136B2

(12) United States Patent
Bucher et al.

(10) Patent No.: US 9,606,136 B2
(45) Date of Patent: Mar. 28, 2017

(54) DEVICE AND METHOD FOR TRANSFERRING REACTION VESSELS

(71) Applicant: Roche Diagnostics Operations, Inc., Indianapolis, IN (US)

(72) Inventors: Marco Bucher, Hohenrain (CH); Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 144 days.

(21) Appl. No.: 14/103,257

(22) Filed: Dec. 11, 2013

(65) Prior Publication Data
US 2014/0170636 A1 Jun. 19, 2014

(30) Foreign Application Priority Data

Dec. 19, 2012 (EP) .................................... 12198235

(51) Int. Cl.
*G01N 35/04* (2006.01)
*G01N 35/00* (2006.01)
*G01N 35/02* (2006.01)

(52) U.S. Cl.
CPC ......... *G01N 35/04* (2013.01); *G01N 35/0099* (2013.01); *G01N 35/025* (2013.01); *G01N 35/026* (2013.01); *Y10T 436/114165* (2015.01)

(58) Field of Classification Search
CPC ............. G01N 35/0099; G01N 35/025; G01N 35/026; G01N 35/04; G01N 2035/0439; G01N 2035/0474; G01N 2035/0441; G01N 2035/0444; G01N 2035/0446; G01N 2035/0465; Y10T 436/114165
See application file for complete search history.

(56) References Cited

U.S. PATENT DOCUMENTS 5,183,638 A * 2/1993 Wakatake .......... G01N 35/0098
366/218
5,305,650 A * 4/1994 Koike ...................... G01N 1/28
73/864.21
5,782,515 A * 7/1998 Jehan ................... B25J 15/0206
294/185

(Continued)

FOREIGN PATENT DOCUMENTS

EP  1873531 A2  1/2008
EP  2495571 A2  9/2012

(Continued)

*Primary Examiner* — Natalie Huls
(74) *Attorney, Agent, or Firm* — Roche Diagnostics Operations, Inc.

(57) ABSTRACT

A method and an automated system for testing liquid samples comprising a reaction vessel transferring device are presented. A first analytical unit for running a first diagnostic test comprises a rotatable first vessel holder detachably holding reaction vessels. A second analytical unit for running a second diagnostic test comprises a stationary linear second vessel holder detachably holding reaction vessels. The transferring device comprises a gripper for gripping a reaction vessel and transfers reaction vessels from the first vessel holder to the second vessel holder and/or vice versa. The device is translatable parallel to the second vessel holder and the gripper moves along a curved path between a picking position and a reaction vessel seat of the second vessel holder.

12 Claims, 6 Drawing Sheets

(56) References Cited

U.S. PATENT DOCUMENTS

| | | | |
|---|---|---|---|
| 6,293,750 B1* | 9/2001 | Cohen | G01N 35/0099 414/744.4 |
| 7,141,213 B1* | 11/2006 | Pang | G01N 35/0095 422/65 |
| 8,752,440 B2* | 6/2014 | Tatsutani | G01N 35/026 422/65 |
| 2003/0049170 A1* | 3/2003 | Tamura | B01L 3/0275 422/63 |
| 2004/0245275 A1* | 12/2004 | Yanami | G01N 35/0092 221/197 |
| 2007/0172390 A1* | 7/2007 | Ootani | G01N 35/0099 422/64 |
| 2008/0044311 A1* | 2/2008 | Iguchi | G05D 23/2424 422/63 |
| 2008/0063567 A1 | 3/2008 | Schacher et al. | |
| 2008/0241939 A1* | 10/2008 | Matsuo | G01N 35/1002 436/54 |
| 2008/0318323 A1* | 12/2008 | Shintani | B01L 3/5082 436/47 |
| 2009/0220379 A1* | 9/2009 | Wakamiya | G01N 35/00594 422/65 |
| 2010/0028203 A1* | 2/2010 | Frey | G01N 35/0099 422/65 |
| 2010/0178205 A1 | 7/2010 | Matsuyama | |
| 2010/0233754 A1* | 9/2010 | Guex | G01N 35/02 435/29 |
| 2010/0261595 A1 | 10/2010 | Schaefer et al. | |
| 2011/0150609 A1* | 6/2011 | Ford | G01N 35/0099 414/222.07 |
| 2011/0293475 A1* | 12/2011 | Rosenberg | G01N 35/025 422/64 |
| 2013/0239527 A1* | 9/2013 | Clarke | B01L 3/50825 53/492 |
| 2014/0311090 A1* | 10/2014 | Weber | B67B 7/182 53/381.4 |
| 2015/0132798 A1* | 5/2015 | Fox | G01N 35/0095 435/40.5 |
| 2015/0142171 A1* | 5/2015 | Li | B25J 9/1692 700/251 |
| 2015/0160250 A1* | 6/2015 | Bucher | G01N 35/0099 436/48 |

FOREIGN PATENT DOCUMENTS

| | | |
|---|---|---|
| GB | 2440269 A | 1/2008 |
| JP | 2001-013151 A | 1/2001 |
| WO | 2010/078177 A1 | 7/2010 |

* cited by examiner

DEVICE AND METHOD FOR TRANSFERRING REACTION VESSELS

CROSS-REFERENCE TO RELATED APPLICATIONS

This application is a continuation of EP 12198235.9, filed Dec. 19, 2012, which is hereby incorporated by reference.

BACKGROUND

The present disclosure generally relates to the field of analytical sample processing and, in particular, to a device, system and process for transferring reaction vessels for analytical sample processing.

In recent years, clinical analyzers offering a broad variety of analytical methods have become commercially available. Depending on the specific analyzer used, samples can be tested by various diagnostic methods in an automated manner.

As a matter of fact, depending on the number of analytical units, analyzers can have a comparably large footprint. Furthermore, since the analytical methods may differ in cycle times as given by the time required for processing one sample, the processing of samples can be blocked until an on-going run of analytical method is completed. Therefore, the processing of samples can be rather time-consuming.

In light of the foregoing, there is a need to improve conventional clinical analyzers provided with a number of analytical units offering various analytical methods by having an analyzer with a comparably small footprint available which also allows for time- and cost-efficient sample processing.

SUMMARY

According to the present disclosure, an automated system and method for testing liquid samples is presented. The automated system can comprise a first analytical unit for carrying out at least one first diagnostic test comprising a rotatable first vessel holder having a plurality of reaction vessel seats for detachably holding reaction vessels; a second analytical unit for carrying out at least one second diagnostic test comprising a stationary linear second vessel holder having a plurality of reaction vessel seats for detachably holding reaction vessels; and a reaction vessel transferring device. The reaction vessel transferring device can comprise at least one gripper for gripping a reaction vessel and transferring reaction vessels from the first vessel holder to the second vessel holder and/or from the second vessel holder to the first vessel holder, wherein the reaction vessel transferring device is translatable parallel to the second vessel holder; a first part comprising a linearly translatable socket; and a second build-up part, rotatably attached to the linearly translatable socket and having a guiding element which is brought in engagement with a guiding path to control rotation of the second build-up part with respect to the linearly translatable socket. The gripper can be attached to the second build-up part and can move at least in part along a curved path between a picking position and at least one reaction vessel seat of the second vessel holder by linear translation of the linearly translatable socket.

Accordingly, it is a feature of the embodiments of the present disclosure to improve conventional clinical analyzers provided with a number of analytical units offering various analytical methods by having an analyzer with a comparably small footprint available which also allows for time- and cost-efficient sample processing. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
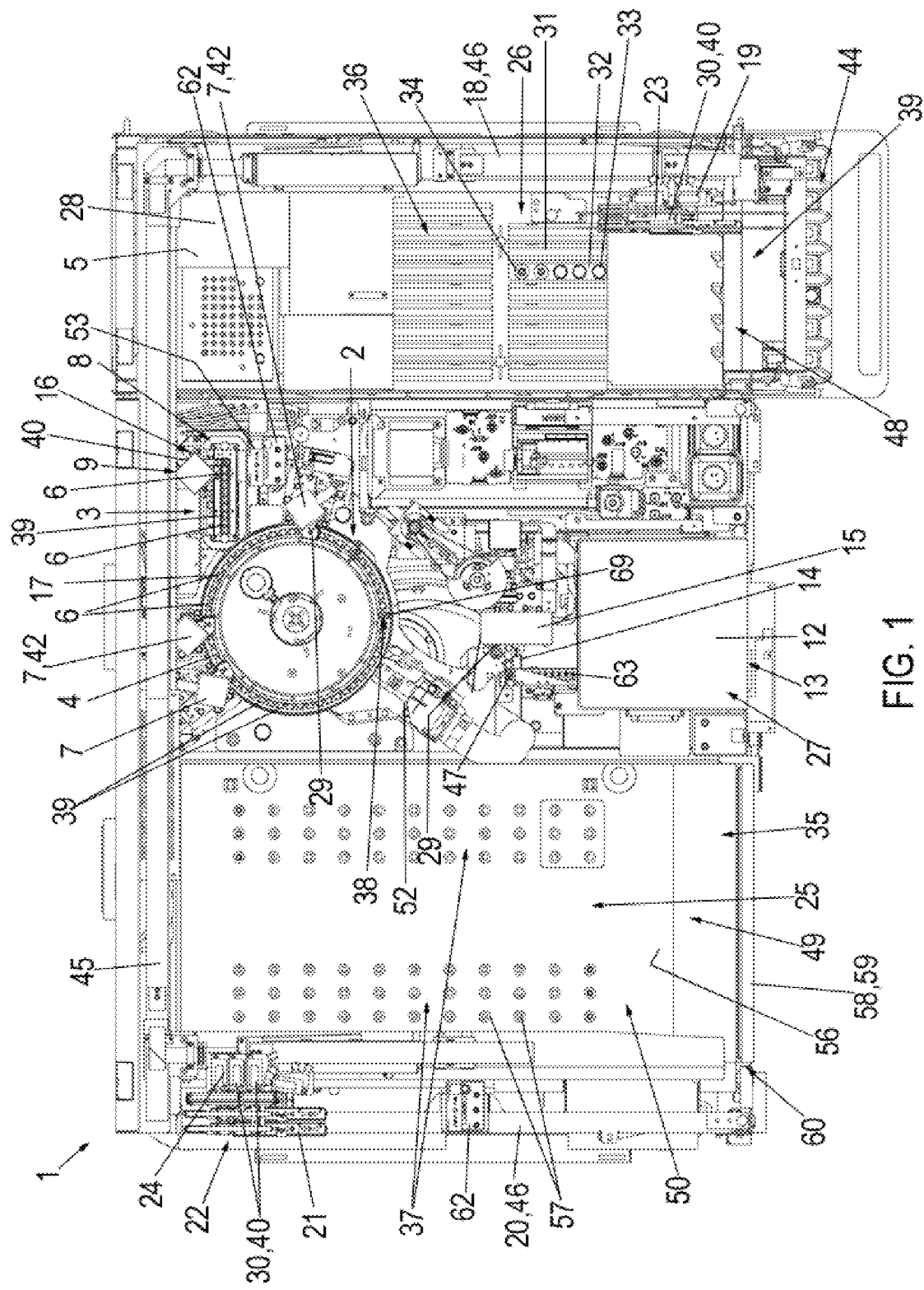
FIG. 1 illustrates a top view of a system for testing liquid samples according to an embodiment of the present disclosure.
Figure 2:
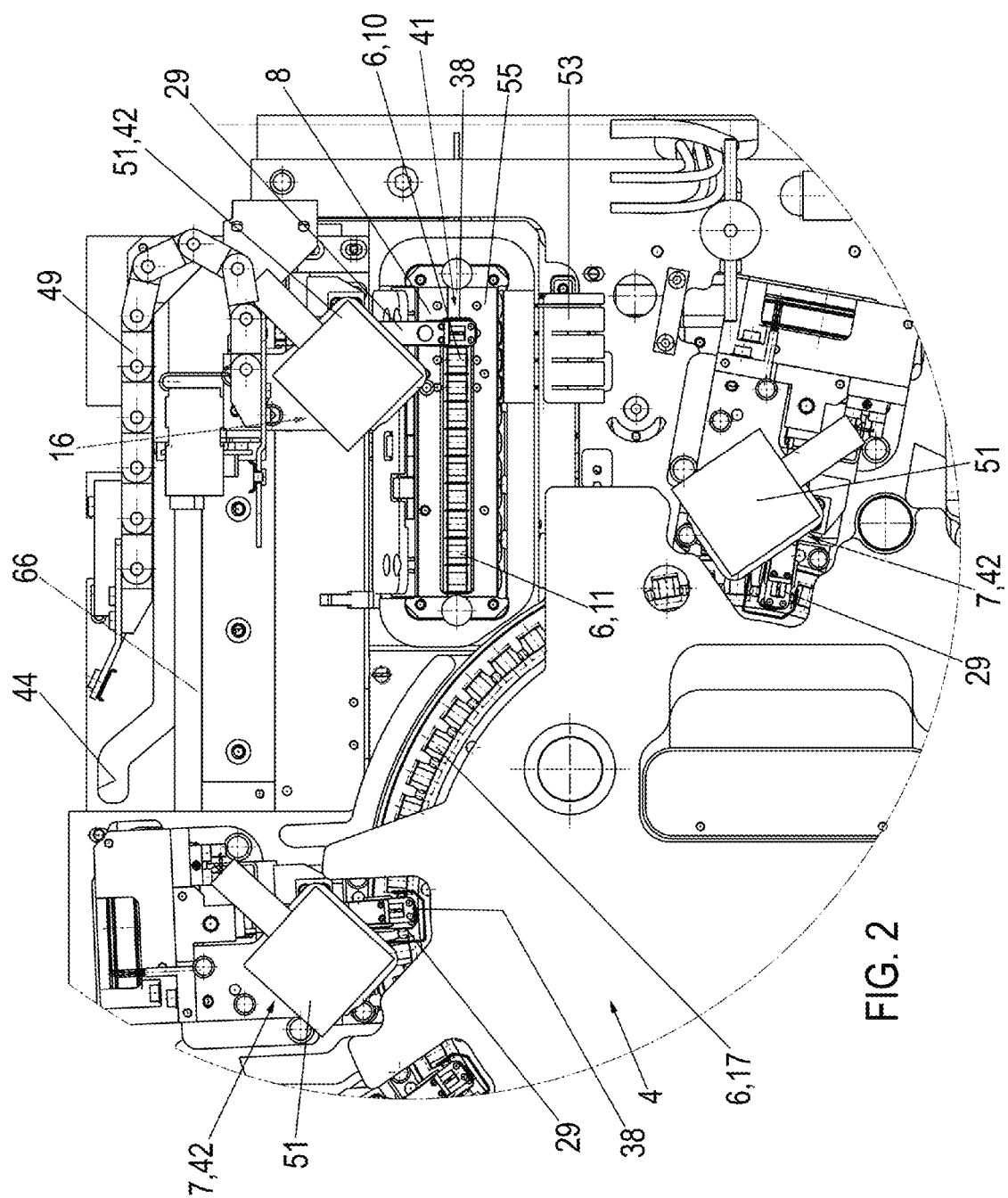
FIG. 2 illustrates a top view of an enlarged detail of the system of FIG. 1 according to an embodiment of the present disclosure.
Figure 3:
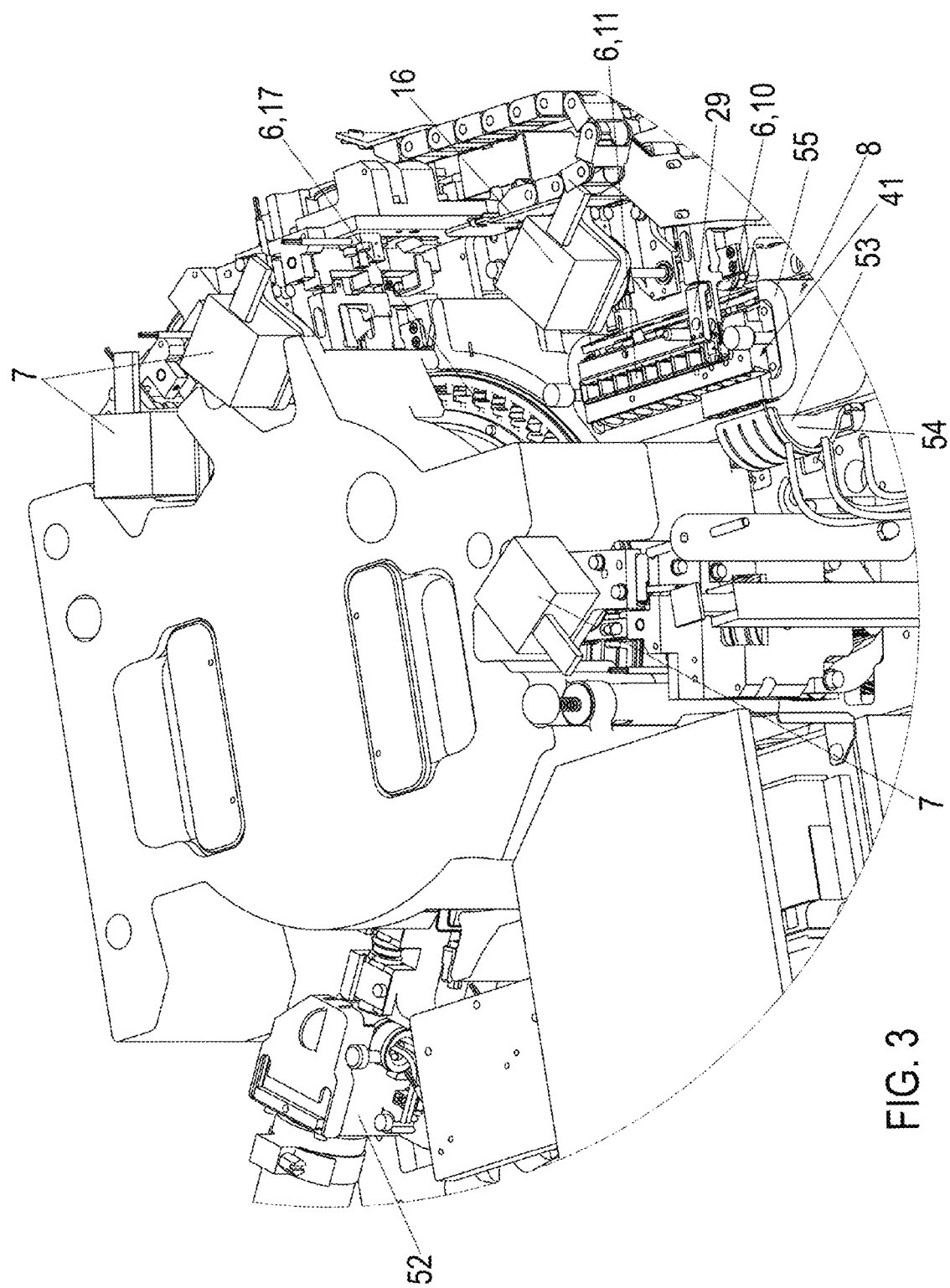
FIG. 3 illustrates a perspective view of another enlarged detail of the system of FIG. 1 according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A new reaction vessel transferring device for an automated system for testing liquid samples is presented. The device can be configured in various ways in accordance with specific demands of the user and, for example, can be particularly useful in connection with automated analyzers for analyzing samples by various analytical methods such as, but not limited to, clinical-chemical and coagulation tests.

The term "sample", as used herein, can refer to a material suspected of containing one or more analytes of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The sample can be pre-treated prior to use, such as preparing plasma from blood, diluting viscous fluids, lysis or the like. Methods of treatment can involve filtration, distillation, concentration, inactivation of interfering components, and the addition of reagents. A sample may be used directly as obtained from the source or following a pre-treatment to modify the character of the sample, for example, after being diluted with another solution or after having been mixed with reagents, for example, to carry out one or more diagnostic assays like clinical chemistry assays, immunoassays, coagulation assays, nucleic acid testing, etc. The term "sample" as used herein is therefore not only used for the original sample but can also relate to a sample which has already been processed (pipetted, diluted, mixed with reagents, enriched, having been purified, having been amplified and the like).

The term "reagent" as used herein can indicate a composition required for treatment of a sample. Reagents may be any liquid, for example, a solvent or chemical solution, which needs to be mixed with a sample and/or other reagent in order for example, for a reaction to occur, or to enable detection. A reagent may be for example a diluting liquid, including water, it may comprise an organic solvent, it may comprise a detergent, and it may be a buffer. Reagents may also be dry reagents adapted, for example, to be dissolved by a sample, another reagent or a diluting liquid. A reagent in the more strict sense of the term may be a liquid solution containing a reactant, typically a compound or agent capable for example, of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, and the like. According to one embodiment, reagents can form homogeneous mixtures with samples and can carry out homogeneous assays. According to another embodiment, reagents can be heterogeneously mixed with samples and can therefore carry out heterogeneous assays. An example of heterogeneous assay can be a heterogeneous immunoassay. Some of the reactants, for example, capturing antibodies, can be immobilized on a solid support. Examples of solid supports can be streptavidin coated beads, for example, magnetic beads, or latex beads suspended in solution, used, for example, in latex agglutination and turbidimetric assays.

According to one embodiment, the system for use with the reaction vessel transferring device can comprise a first analytical unit for carrying out at least one first diagnostic test. The first analytical unit can comprise a rotatable first vessel holder having a plurality of reaction vessel seats for detachably holding reaction vessels. In one embodiment, the system can comprise a second analytical unit for carrying out at least one second diagnostic test. The second analytical unit can comprise a substantially stationary linear second vessel holder having a plurality of reaction vessel seats for detachably holding reaction vessels.

As used herein, the term "analytical unit" can relate to a functional (and optionally structural) entity that carries out one or more diagnostic tests. In one embodiment, each of the first and second analytical units can be a modular unit.

As used herein, the term "vessel holder" can relate to any device capable of holding one or more sample vessels in dedicated vessel positions, wherein each sample vessel can be held in one vessel position as given by a region of the vessel holder adapted for removably holding one sample vessel. The first vessel holder can be a rotor which can be rotated so as to bring reaction vessels loaded thereon at different angular positions. Contrary thereto, the second vessel holder can be kept stationary with respect to the first vessel holder so that the first vessel holder can be rotated with respect to the second vessel holder. In one embodiment, the second vessel holder can have a substantially linear arrangement of holding seats, each of which can hold one reaction vessel.

As used herein, the term "reaction vessel" can relate to any device capable of containing liquids such as samples and reagents. In one embodiment, the reaction vessel can be a cuvette. The term "cuvette" as used herein can indicate a vessel comprising a body at least in part optically transparent to receive liquids in an inner space and to allow the photometric measurement of a liquid sample contained therein, i.e., the measurement of changes in optical transmission, such as absorbance and scattering, used in the optical analysis of analytes present in a sample. The cuvette may be used in the performance of scattering assays to detect the result of a chemical or biological reaction or to monitor the progress of a chemical or biological reaction, for example, in a coagulation assay, agglutination assay, turbidimetric assay. According to one embodiment, the cuvette body can comprise side walls, a closed bottom and an upper opening for allowing liquids to be introduced in the inner space formed by the side walls and the closed bottom. According to one embodiment, the cuvette can comprise at least one lip projecting outwards of the cuvette body in proximity of the upper opening. This lip may be convenient when handling the cuvette and/or for holding the cuvette in a cuvette holding position. According to one embodiment, the cuvette can be manufactured in one piece by injection moulding polymeric material. According to one embodiment, the volume can be below about 1 mL and can receive a volume of liquid below about 0.5 mL. According to one embodiment, the body can comprise side walls and two openings to allow liquid to flow through. The cuvette may thus be embodied as a channel, tube, capillary flow-through vessel and the like. The cuvette may have an inner volume in the milliliter or microliter range.

In one embodiment, a cycle time (i.e., time for processing one sample) of the second diagnostic test can be longer than a cycle time of the first diagnostic test. Specifically, in one embodiment, the second diagnostic test can be a coagulation test and the first diagnostic test can be related to determining clinical-chemical parameters of the samples.

In one embodiment, the reaction vessel transferring device can comprise at least one gripper for gripping one reaction vessel and can transfer reaction vessels from the first vessel holder to the second vessel holder and/or from the second vessel holder to the first vessel holder.

In one embodiment, the gripper can move along the stationary second vessel holder. Accordingly, individual reaction vessels can readily be transferred from the first vessel holder (rotor) to any reaction vessel seat of the second vessel holder and/or from one reaction vessel seat of the second vessel holder to the rotor.

In one embodiment, the gripper can move at least in part along a curved path (along an at least partially curved path) for transferring reaction vessels between the first and second vessel holders. In one embodiment, the gripper can be moved between a picking position for picking one reaction vessel supported by one reaction vessel seat of the first vessel holder and at least one reaction vessel seat of the second vessel holder. Accordingly, the second vessel holder can be positioned non-tangentially with respect to the rotatable first vessel holder so as to reduce the footprint of the system.

In one embodiment, the reaction vessel transferring device can comprise a first part comprising a substantially linearly translatable socket, and a second part herein referred to as "build-up", rotatably attached to the socket and having a guiding element which can be brought in engagement with a guiding path so as to control rotation of the build-up with respect to the socket. The gripper can be attached to the build-up. Accordingly, the build-up can be translated together with the socket and the gripper can readily be rotated with respect to the socket by substantially linear translation of the socket.

In one embodiment, the reaction vessel transferring device can comprise a resilient device for pre-tensioning the build-up in rotation against the socket. Accordingly, control of the rotational movement of the gripper can be facilitated. Generally, the reaction vessel transferring device can be made compact in shape and can be manufactured in an easy and cost-effective manner since the socket needs to be only linearly translatable, with the build-up automatically rotated with respect to the socket while substantially linearly translating the socket.

In one embodiment, the gripper can be coupled to a mixing/shaking mechanism for mixing and/or shaking liquids contained in a gripped reaction vessel. Accordingly, liquids can be mixed and/or shaken when being gripped by the gripper so as to save cost and time when processing samples.

A method can be configured in various ways in accordance with specific demands of the user and, for example, can be used in connection with automated analyzers having various analytical methods. Specifically, the method can be used in a system or instrument using a reaction vessel transferring device as above-described.

In one embodiment, the method can comprise transferring reaction vessels from the first vessel holder to the second vessel holder and/or transferring reaction vessels from the second vessel holder to the first vessel holder. In one embodiment, the transfer of reaction vessels can comprise translating the reaction vessels substantially parallel to the second vessel holder and moving the reaction vessels at least in part along a curved path (along an at least partially curved path) between a picking position for gripping one reaction vessel in a reaction vessel seat of the first vessel holder and at least one reaction vessel seat of the second vessel holder.

In one embodiment, the method can further comprise transferring one reaction vessel from one incubation seat of the second vessel holder for incubating one sample and one or more reagents to one test seat of the second vessel holder for carrying out the second diagnostic test.

In one embodiment, the method can further comprise gripping the reaction vessel. One sample and/or one or more reagents can be pipetted into the gripped reaction. Liquids can be mixed in the gripped reaction vessel.

In one embodiment, one sample and one or more reagents contained in one reaction vessel can be mixed during transfer of the reaction vessel from one incubation seat to one test seat.

Referring initially to FIGS. 1-5, FIGS. 1-5 depict various views of an integrated system for testing liquid samples generally referred to as reference numeral 1. In one embodiment, the system 1 can be an automated stand-alone instrument which can be placed on a workbench.

Specifically, the system 1 can comprise a first analytical unit 2 and a second analytical unit 3 for testing liquid samples. The first analytical unit 2 can carry out first diagnostic tests related to clinical-chemistry. As illustrated, in one embodiment, the first analytical unit 2 can comprise a motor-driven rotor 4 rotatably fixed to a base 5 so as to be rotated with respect to the base 5. On the outer periphery, the rotor 4 can have a ring-like arrangement of reaction vessel seats 6, each of which can detachably hold one reaction vessel 38 such as, but not limited to, a cuvette, to receive liquid sample and/or one or more reagents. Accordingly, reaction vessels 38 can be put into the vessel seats 6 or removed therefrom according to the specific demands of the user. The reaction vessel seats 6 of the rotor 4 can be brought to a pre-determined temperature according to the specific demands of the user so as to improve reaction rates between samples and reagents contained in the reaction vessels 38.

The first analytical unit 2 can further comprise a plurality of first workstations 7, to carry out one or more processing steps related to clinical-chemistry and can, for example, mix and pipette fluids and can detect body substances which can be used to examine bodily fluids. Clinical-chemical sample processing is well-known to those of skill in the art so that it is not necessary to elucidate it further herein. As illustrated, in one embodiment, the first workstations 7 can be arranged along the outer circumference of the rotor 4 so that reaction vessels 38 loaded on the rotor 4 can be readily accessed.

Specifically, as illustrated in FIG. 1, in one embodiment, the first analytical unit 2 can comprise a plurality of first workstations 7 configured, inter alia, as mixing stations for mixing liquids contained in reaction vessels 38 and one clinical-chemistry test photometer 52 for optically measuring various clinical-chemical test parameters of the samples. Stated more particularly, in one embodiment, each first workstation 7 can comprise a movable gripper 29, for gripping one reaction vessel 38, lifting the reaction vessel 38 from the reaction vessel seat 6, agitating the reaction vessel 38 for mixing liquids contained therein, and placing the reaction vessel 38 on a reaction vessel seat 6 of the rotor 4. For being gripped by the gripper 29, each reaction vessel 38 can, for example, comprise an upper collar. For mixing of reaction vessels 38, the gripper 29 can be coupled to a mixing mechanism 42 driven by a motor 51. Accordingly, the gripper 29 can have a double functionality of gripping reaction vessel 38 and mixing liquids contained therein.

The clinical-chemistry test photometer 52 can comprise a light-generating device, to generate light of one or more wavelengths and a light-detecting device arranged in a manner to detect photometrically clinical-chemical test parameters of samples contained in the reaction vessels 38. The light-generating device can, for example, comprise one or more diodes and one or more lamps. The light-detecting device can, for example, comprise a charge coupled device (CCD), photo-diode array, photomultiplier tube array, charge injection device (CID), CMOS detector, avalanche photo diode and the like. The clinical-chemistry test photometer 52 can further include light guiding elements such as, but not limited to, optical fibres, lenses and mirrors and/or light separating elements such as, but not limited to, transmission gratings, reflective gratings and prisms. The clinical-chemistry test photometer 52 can be arranged in such a manner that light having passed through a reaction vessel 38 can be detected by the photometer 52. Detection can be done by bringing one cuvette at a time to the photometer 52 while rotating the rotor. According to one embodiment, this detection can be done on-the-fly, i.e., while the rotor 4 is rotated. Accordingly, in the system 1, by rotating the rotor 4, individual reaction vessels 38 can be moved to the first workstations 7 for pipetting and mixing of samples and reagents contained therein to then be moved to the clinical-chemistry test photometer 52 for optical sample testing. Corresponding to the number of first workstations 7, different reaction vessels 38 can simultaneously be processed. While in FIG. 1 a number of three first workstations 7 and one clinical-chemistry test photometer 52 are shown for the purpose of illustration only, those of skill in the art will appreciate that any other number of first workstations 7 and clinical-chemistry test photometers 52 can be envisaged according to the specific demands of the user.

The second analytical unit 3 can carrying at least one second diagnostic test different from the first diagnostic tests which, in one embodiment, can relate to a coagulation test involving optical measurements of the samples. Specifically, as illustrated in FIG. 1, in one embodiment, the second analytical unit 3 can comprise a substantially linear incubation block 8 fixedly secured to the base 5 so that the rotor 4 can be rotated with respect to the incubation block 8 kept stationary. As illustrated, the incubation block 8 can have a substantially linear arrangement of reaction vessel seats 6, each of which can receive one reaction vessel 38. Accordingly, reaction vessels 38 can be put on the reaction vessel seats 6 or removed therefrom according to the specific demands of the user. The linear incubation block 8 can advantageously allow parallel sample pipetting and parallel sample detection in a facilitated and optimized optical setup wherein only one linear movement may be required for translating reaction vessels 38 to the various reaction vessel seats 6. Since reaction vessels 38 do not undergo a movement while seated in the incubation block 8 (which would be the case when placed on the rotor 4), reliability of coagulation tests of samples can be improved. The incubation block 8 can have a compact shape and can be manufactured in a time- and cost-effective manner.

The reaction vessel seats 6 of the incubation block 8 can be brought to a pre-determined temperature so as to incubate (i.e., heating with a specific temperature for a specific time interval) samples and reagents contained in the reaction vessels 38. Heating of the samples can, for example, be performed by electric heating such as a heating foil comprising heating wires. Except from an upper side, the incubation block 8 can be encased by thermally isolating material.

As illustrated, in one embodiment, the linear arrangement of reaction vessel seats 6 can comprise plural (for example, three) test seats 10, one reference seat 41 and a plurality (for example, seven) of incubation seats 11 wherein each test seat 10 can be coupled to a coagulation test photometer 53 for optically testing samples. Specifically, in one embodiment, the coagulation test photometer 53 can comprise a light-generating device to generate light to perform an optical measurement of the samples and a light-detecting device for detecting light transmitted through the samples. In one embodiment, light fibres 54 can be used to direct the light to the reaction vessels 38 placed on the test seats 10. Due to the linear arrangement of reaction vessel seats 6, light generated by the coagulation test photometer 53 can readily be directed to the test seats 10 via the light fibres 54. Accordingly, a plurality (for example, three) of samples can simultaneously be tested and a plurality (for example, seven) of sample/reagent mixtures can be incubated prior to testing. The cycle time, i.e., the time required for processing one sample, by a coagulation test usually is longer than the cycle time of testing clinical-chemical parameters. Accordingly, samples usually stay longer in the second analytical unit 3 than in the first analytical unit 2. Furthermore, due to the fact that samples can be kept stationary during incubation, a detrimental influence on coagulation tests can be avoided by seating reaction vessels 38 for incubation of samples in the stationary incubation block 8. The substantially linear arrangement of reaction vessels seats 6, in particular test seats 10, can allow for an easy and quick transport of reaction vessels 38 between reaction vessel seats 6. Furthermore, optical properties of samples can readily be determined, for example, in parallel due to an easy adjustment of the optical components.

The second analytical unit 3 can further comprise a reaction vessel transferring device 16, for transferring reaction vessels 38 from the rotor 4 to the incubation block 8 and from the incubation block 8 to the rotor 4. Specifically, in one embodiment, the reaction vessel transferring device 16 can comprise a movable gripper 29, for gripping one reaction vessel 38 and transferring the reaction vessel 38 between a first picking position 17 at the rotor 4 (i.e., reaction vessel seat 6 of the rotor 4) and the linear incubation block 8. As used herein, the term "first picking position" can be related to a specific position of the gripper 29 in which the gripper 29 can have an appropriate (radial) position with respect to a rotational axis of the rotor 4 (i.e., gripper 29 can be in substantially orthogonal arrangement with respect to the outer circumference of the rotor 4). Accordingly, reaction vessels 38 can readily be removed or placed on the rotor 4. By rotating the rotor 4, reaction vessels 38 loaded on the rotor 4 can be moved to the first picking position 17 for gripping by the reaction vessel transferring device 16. The reaction vessel transferring device 16 is further detailed below with respect to FIGS. 2 to 5.

With continued reference to FIG. 1, the system 1 can further comprise a loading/unloading unit 27 for loading/unloading reaction vessels 38 to/from the rotor 4. Specifically, in one embodiment, the loading/unloading unit 27 can comprise a reaction vessel feeder 12, to receive a plurality of reaction vessels 38 which can be loaded to the reaction vessel feeder 12 via a reaction vessel loading area 13. The reaction vessel feeder 12 can thus serve as a reservoir for storing reaction vessels 38 in bulk. In one embodiment, the reaction vessel feeder 12 can be configured for individualizing reaction vessels 38 and transporting individualized reaction vessels 38 to a handover position 14 via a transport rail 63.

As illustrated in FIG. 1, in one embodiment, the loading/unloading unit 27 can further comprise an input/output workstation 15 for transporting reaction vessels 38 from the handover position 14 to a second picking position 69 (i.e., reaction vessel seat 6 of the rotor 4) and from the second picking position 69 to a waste position 47. In one embodiment, the input/output workstation 15 can have a movable gripper 29 capable of gripping one reaction vessel 38 in handover position 14 and transporting the reaction vessel 38 to the second picking position 69 on the rotor 4. As used herein, the term "second picking position" can be related to a specific position of the gripper 29 of the input/output workstation 15 in which the gripper 29 can have an appropriate position for gripping one reaction vessel 38 loaded on the rotor 4. Furthermore, the gripper 29 can grip one reaction vessel 38 in second picking position 69 on the rotor 4 and transport the reaction vessel 38 to the waste position 47. In waste position, used reaction vessels 38 can fall into a vessel waste. Accordingly, in the system 1, reaction vessels 38 can be transported from the handover position 14 to the rotor 4 and from the rotor 4 to the waste position 47 by operating the gripper 29 of the input/output workstation 15.

The system 1 can further comprise a sampling unit 26 for receiving samples to be tested by the first and/or second analytical units 2, 3. As illustrated in FIG. 1, in one embodiment, the sampling unit 26 can comprise a sample storage area 36 provided with plural rack seats 31, each of which can receive one sample rack 32 for holding a plurality of sample vessels 33 such as, but not limited to, sample tubes. In one embodiment, each sample rack 32 can comprise a linear arrangement of, for example, five, sample vessel seats 34, with each sample vessel seat 34 holding one sample vessel 33.

Specifically, as illustrated, in one embodiment, the samples can be manually or automatically loaded/unloaded to/from a front-sided sample loading area 39 coupled to a rack transport mechanism 48 for transporting individual sample racks 32 between the sample loading area 39 and the sample storage area 36. Furthermore, the sampling unit 26 can have a reader 50 (for example, barcode scanner or RFID reader) to identify sample racks 32 and/or sample vessels 33 by reading information stored in machine-readable information tags attached to the sample racks 32 and/or sample vessels 33.

The system 1 can further comprise a reagent compartment 25 for storing reagents related to the first and second diagnostic tests. Specifically, as illustrated in FIG. 1, in one embodiment, the reagent compartment 25 can comprise a reagent storage area 37 provided with reagent containers containing reagent. Stated more particularly, in one embodiment, the reagent storage area 37 can comprise a plurality of reagent container seats for receiving reagent containers which can be arranged in shelf-like storages ("warehouse"), wherein a reagent container handler can be arranged between the shelf-like storages for transporting individual reagent containers.

Specifically, FIG. 1 depicts a top cover 56 of the reagent storage area 37 made of isolating material with a plurality of pipetting holes 57 for pipetting of reagents contained in reagent containers placed below the top cover 56 (i.e., placed on a highest level of two shelf-like storages). Accordingly, reagent containers can be stored in different levels of the shelf-like storages and can be positioned at the highest level when needed. In one embodiment, the reagent compartment 25 can be actively cooled so that reagents can be stored therein for an extended period of time. In order to keep the reagents at a pre-determined (low) temperature, the reagent compartment 25 can be encased by thermally isolating material.

As further illustrated in FIG. 1, in one embodiment, reagent containers can be manually or automatically loaded/unloaded to/from a front-sided reagent loading area 35. Specifically, in one embodiment, the reagent compartment 25 can comprise a drawer 58 with a handle 59 so that the drawer 58 can readily be pulled out of a frame 60 or pushed in, respectively. When pulling the drawer 58 out of the frame 60, the reagent loading area 35 can be accessible from outside so as to load reagent containers thereon and to remove used reagent containers, respectively. Furthermore, the reagent compartment 25 can have a reader 50 (such as, for example, a barcode scanner or RFID reader) which can be used to identify reagent containers by reading information stored in a machine-readable information tag attached to the reagent containers. Accordingly, information related to the reagents such as, but not limited to, the sort of reagents, expiration dates and the like can be read to assist the automatic handling of the reagent containers. In one embodiment, the reader 50 can read information from information tags while transporting reagent containers in the reagent storage compartment 25. In one embodiment, the reader 50 can read information from information tags attached to reagent containers positioned in the reagent loading area 35 and/or reagent storage area 37.

With continued reference to FIG. 1, the system 1 can also comprise a pipetting unit 22 for pipetting liquids which, in one embodiment, can comprise a first pipettor 23 and a second pipettor 24 coupled to a first transfer mechanism 18 and a second transfer mechanism 20, respectively, for being transported relative to the base 5. Stated more particularly, in one embodiment, each of the transfer mechanisms 18, 20 can comprise one (jointly used) stationary beam 45 and one movable beam 46 substantially orthogonally arranged with and movable along the stationary beam 45. Specifically, in one embodiment, a first transfer head 19 carrying the first pipettor 23 can be fixed to the one movable beam 46 and a second transfer head 21 carrying the second pipettor 24 can be fixed to the other movable beam 46, with each transfer head 19, 21 movable along the respective movable beam 46. Accordingly, the transfer heads 19, 21 can respectively be moved along the stationary beam 45 by moving the movable beam 46 along the stationary beam 45 and can also be moved along the movable beam 46 so as to have components of movement in two directions of travel in a horizontal plane over the base 5. Furthermore, the transfer heads 19, 21 can respectively move in a third direction of travel towards and away from the base 5. Accordingly, the first pipettor 23 and the second pipettor 24 can respectively be moved in a horizontal plane over the base 5 and in vertical direction relative to the base 5.

Each of the first and second pipettors 23, 24 can comprise one or more pipetting channels 30 for pipetting liquids, with each pipetting channel 30 comprising one pipette 40 coupled to a pump for generating a positive or negative pressure therein for discharging and sucking-in liquids, respectively. In one embodiment, the first pipettor 23 can have two pipetting channels 30, one of which can be used for pipetting samples for clinical-chemistry and coagulation tests and the other one can be used for pipetting reagents related to clinical-chemistry. In one embodiment, the second pipettor 24 can have four pipetting channels 30 with four pipettes 40, for example, substantially serially arranged with respect to each other, for pipetting reagents related to the coagulation tests. In one embodiment, at least one of the pipettes 40 of the second pipettor 24 can be heated so as to heat liquids (reagents) contained therein. Accordingly, reagents can be pre-heated before reacting with samples in order to increase reaction rates. The pipettes 40 of the first and second pipettors 23, 24 can, for example, have re-usable metallic needles which can be washed in wash stations 62.

In order to control the various workflows of the system 1, the system 1 can further include a controller 28 which may, for example, be embodied as programmable logic device (microprocessor) running a computer-readable program provided with instructions to perform operations in accordance with predetermined process routines (workflows) for testing liquid samples. For this purpose, the controller 28 can be electrically connected to the various components which can require control and/or provide information including the first and second analytical units 2, 3, the pipetting unit 22, the loading/unloading unit 27 and the reaction vessel transferring device 16.

Referring to FIGS. 2-5, the second analytical unit 3 comprising the reaction vessel transferring device 16 is further described.

Figure 4:
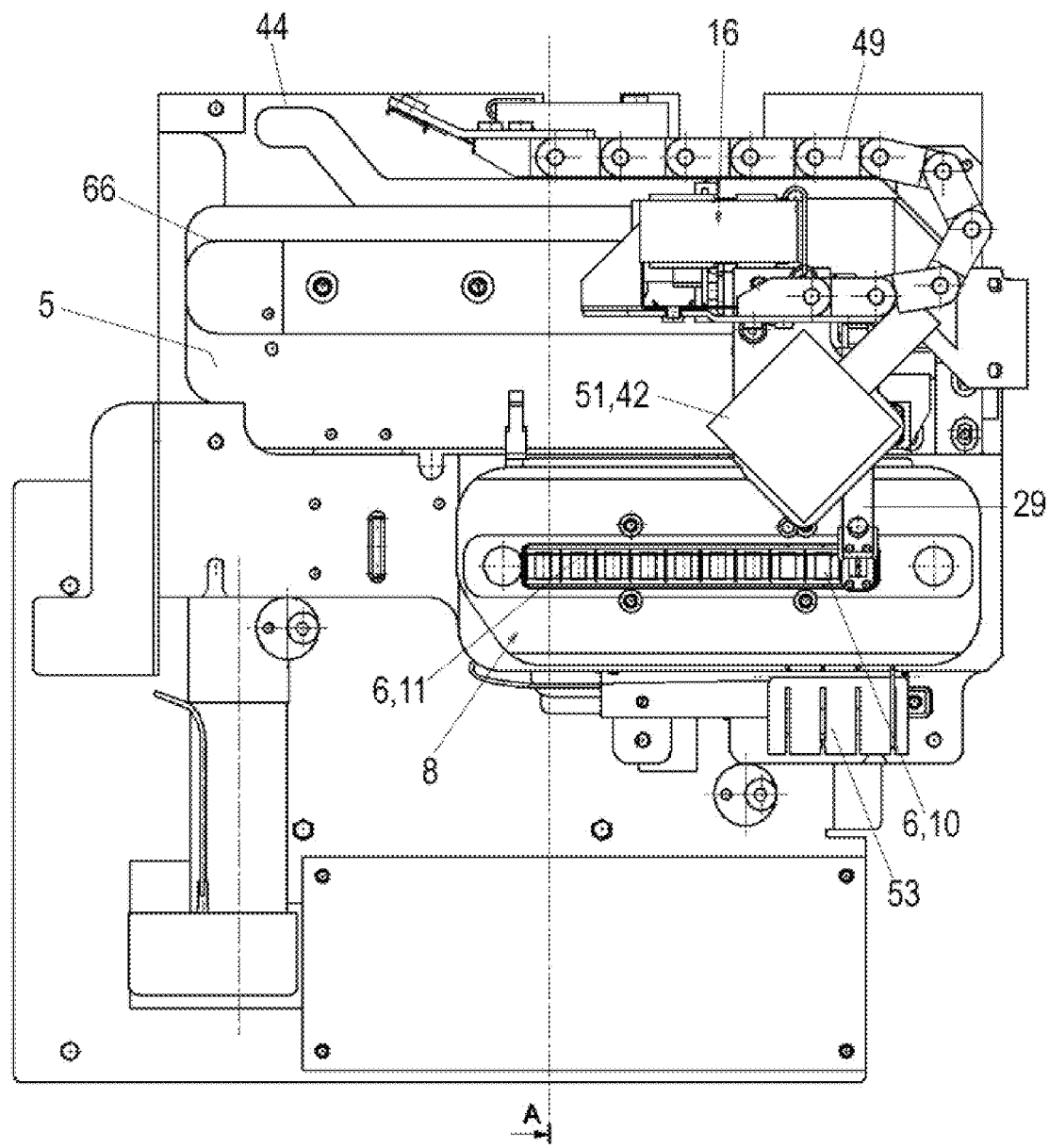
FIG. 4 illustrates a top view of the second analytical unit of the system of FIG. 1 according to an embodiment of the present disclosure.
Figure 5:
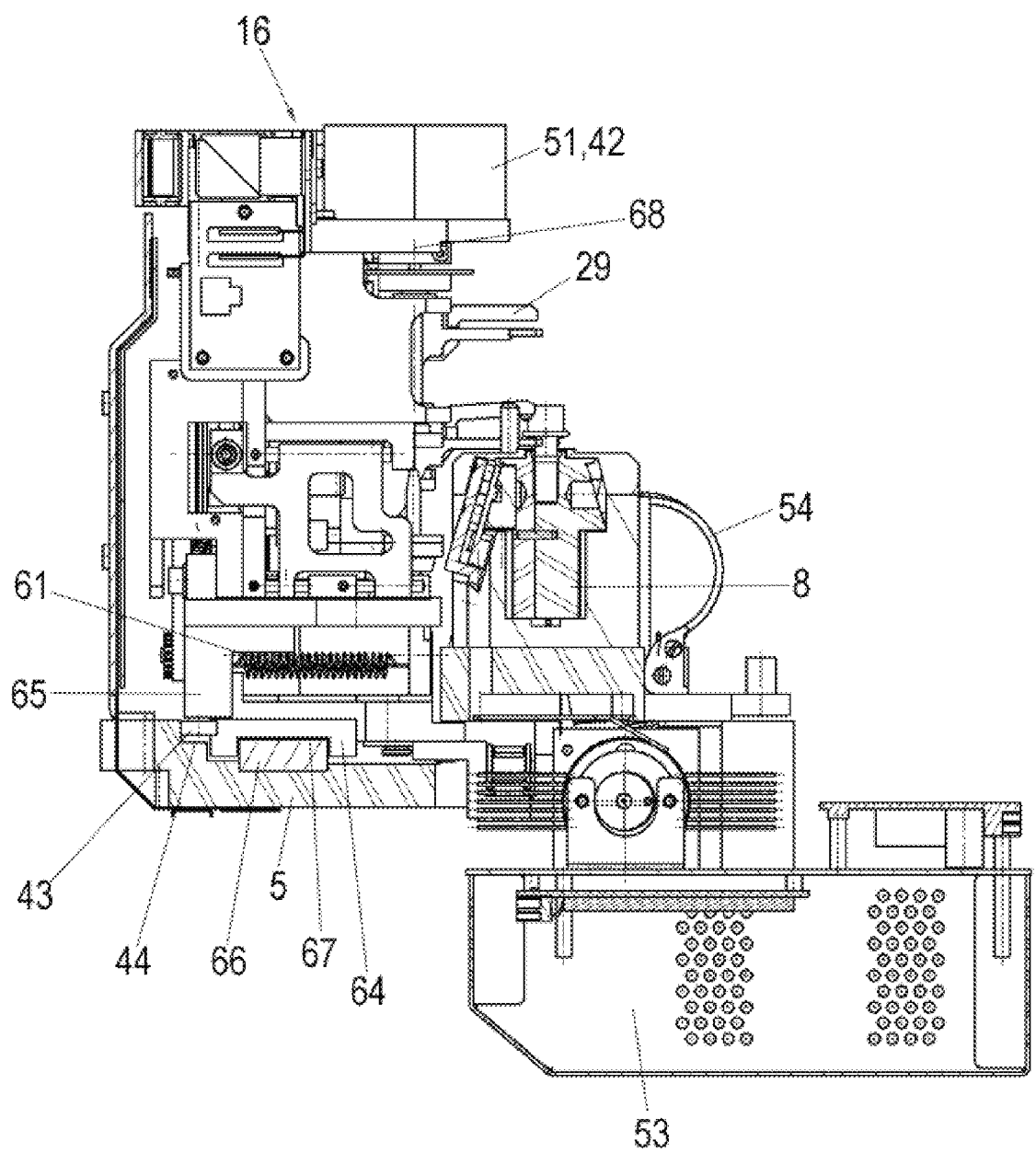
FIG. 5 illustrates a sectional view according to line A-A of FIG. 4 according to an embodiment of the present disclosure.

Accordingly, in one embodiment, the reaction vessel transferring device 16 arranged adjacent the linear incubation block 8 can comprise a socket 64 and a build-up 65 (see FIG. 5) attached to the socket 64 and can have a movable gripper 29 for gripping one reaction vessel 38. As illustrated in FIGS. 4 and 5, a linear guiding rail 66 can be attached to the base 5 in substantially parallel alignment with respect to the linear arrangement of reaction vessels seats 6 of the incubation block 8 for guiding the socket 64. Correspondingly, on the lower side, the socket 64 can have a generally U-shaped recess 67 engaged with the guiding rail 66 so that the socket 64 can be moved along the guiding rail 66. In one embodiment, the socket 64 can slide along the guiding rail 66. In one embodiment, the socket 64 can roll-off the guiding rail 66.

In one embodiment, the build-up 65 can be rotatably fixed to the socket 64 so that the build-up 65 can be rotated around a substantially vertical rotational axis 68 with respect to the socket 64. Specifically, in one embodiment, a resilient member such as, for example, a spring 61 having one end fixed to the socket 64 and the other end fixed to the build-up 65 can be used to pre-tension the build-up 65 in rotation relative to the socket 64. Stated more particularly, by action of the spring 61, the build-up 65 can be pre-tensioned in such a manner that the gripper 29 attached to the build-up 65 can be rotated towards the incubation block 8. Furthermore, in one embodiment, the build-up 65 can have a guiding element 43 which can be brought in engagement with a substantially S-curved guiding groove 44, with the guiding element 43 moving along and guided by the curved guiding groove 44 so as to control the rotational movement of the build-up 65 when translating the socket 64 with respect to the guiding rail 66. In one embodiment, the guiding element 43 can slide along the guiding groove 44. In one embodiment, the guiding element 43 can roll-off the guiding groove 44. Accordingly, when moving the socket 64 along the guiding rail 66, the build-up 65 can be rotated around the rotational axis 68 as controlled by the shape of the guiding groove 44.

As a result, the gripper 29 can be brought in a suitable position both with respect to the reaction vessel seats 6 of the incubation block 8 and with respect to the first picking position 17 for gripping reaction vessels 38. Stated more particularly, controlled by the substantially S-curved path of the guiding groove 44, when translating the socket 64 towards the rotor 4, the gripper 29 can be rotated away from the incubation block 8, then towards the rotor 4, to finally reach a position in which the gripper 29 can be radially aligned with respect to the rotational axis 68 of the rotor 4 (substantially orthogonal to the outer circumference of the rotor 4 and the first picking position 17). Furthermore, when translating the socket 64 away from the rotor 4, the gripper 29 can be rotated towards the incubation block 8 to then return to a position in which the gripper 29 can be substantially orthogonal with respect to the rotor 4 and incubation block 8. Accordingly, with a single translational movement of the socket 64 and rotation of the build-up 65, a time and cost-effective transport of reaction vessels 38 can be reached. Furthermore, a comparably low footprint of the system 1 can be reached.

The gripper 29 can also move in a substantially vertical direction so as to be moved towards and away from reaction vessels 38. For operating the gripper 29, the reaction vessel transferring device 16 can comprise a gripper moving mechanism. A cable chain 49 can protect electric lines for providing electric energy and transmitting control signals.

As illustrated, in one embodiment, the reaction vessel transferring device 16 can have a mixing mechanism 42 operatively coupled to the gripper 29 to agitate one reaction vessel 38 gripped by the gripper 29 similar to the first workstations 7.

In the following, various workflows for testing liquid samples under control of controller 28 are described.

Specifically, in one embodiment, the controller 28 can be set up to control a "coagulation workflow" relating to testing samples with respect to coagulation test parameter and a "clinical-chemistry workflow" relating to testing samples with respect to clinical-chemical test parameters.

Figure 6:
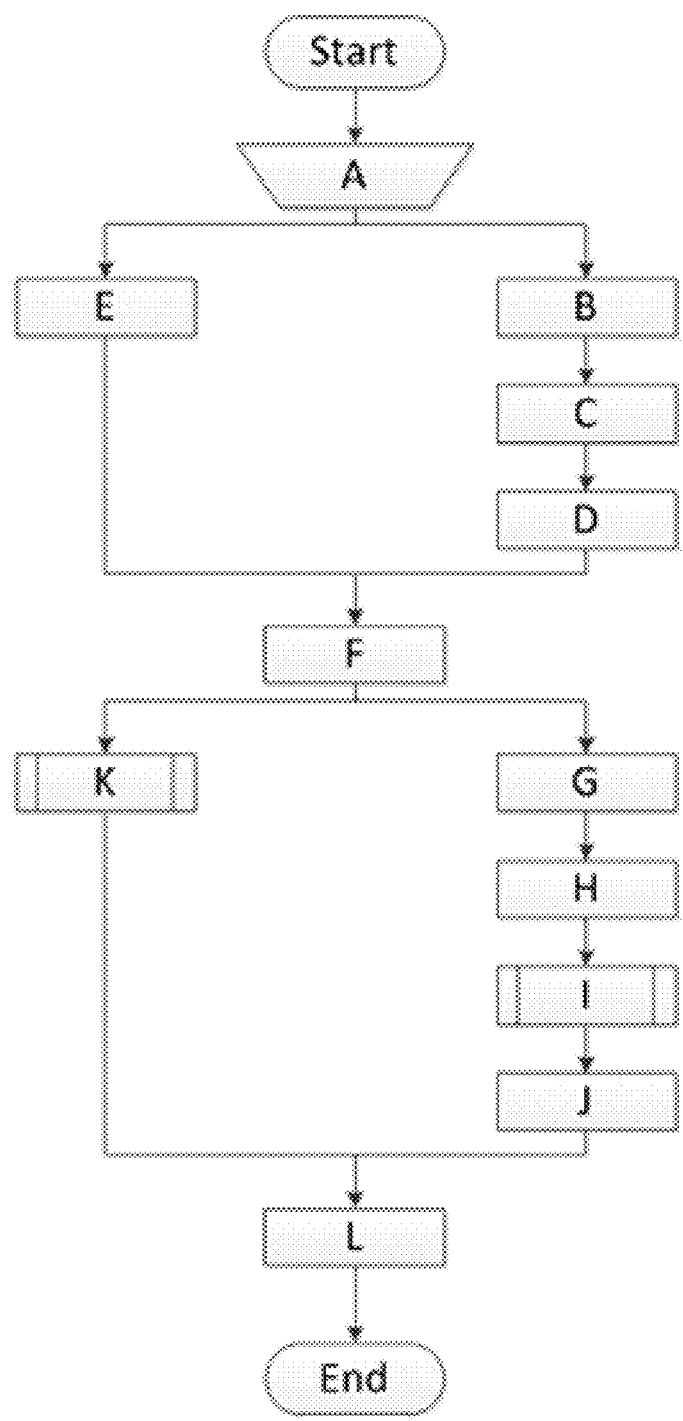
FIG. 6 illustrates a flowchart illustrating various workflows for testing liquid samples with the system of FIG. 1 according to an embodiment of the present disclosure.

With particular reference to FIG. 6, both workflows can start with manually or automatically loading samples, reagents and consumables to the system 1 (step A). Stated more particularly, samples to be tested can be loaded to the sample loading area 39, reagent container related to the first and second diagnostic tests can be loaded to the reagent loading area 35, and reaction vessels 38 such as cuvettes can be loaded to the reaction vessel feeder 12.

Then, in a further step of both workflows, each sample rack 32 can be transported from the sample loading area 39 to the sample storage area 36 by the rack transport mechanism 48 and each reagent container can be transported from the reagent loading area 35 to the reagent storage area 37 by the reagent container handler (step B).

In a further step of both workflows, each sample rack 32 and/or each samples vessel 33 as well as each reagent container can be identified (for example, during transport into the sample storage area 36 and reagent storage area 37, respectively) (step C).

Then, in a further step of both workflows, the sample racks 32 and reagent containers can be positioned in the sample storage area 36 and reagent storage area 37, respectively (step D).

In a further step of both workflows, the reaction vessel feeder 12 can place reaction vessels 38 in the handover position 14 (step E).

Irrespective of using the first or second diagnostic tests, in a further step of both workflows, the reaction vessels 38 can be transferred from the handover position 14 to reaction vessel seats 6 of the rotor 4 by operating the gripper 29 of the input/output workstation 15 and placing reaction vessels 38 on a respective one of the reaction vessel seats 6 brought into the second picking position 69 by rotating the rotor 4 (step F).

In normal use, a plurality of empty reaction vessels 38 can be loaded onto the rotor 4 for testing samples by repeating step E and step F. Furthermore, steps B, C, D, E and F may run at least in part simultaneously.

In case sample testing with respect to coagulation is ordered, for continuing the "coagulation workflow", the rotor 4 can be rotated to bring one empty reaction vessel 38 loaded thereon to the first picking position 17 (step G).

Then, continuing the "coagulation workflow", the reaction vessel 38 in first picking position 17 can be transferred to the incubation block 8 by operating the gripper 29 of the reaction vessel transferring device 16 (step H). Specifically, the gripper 29 can be moved to the first picking position 17, can grip the reaction vessel 38 and can transfer it to an incubation seat 11 of the incubation block 8.

Then, a coagulation test routine embedded in the "coagulation workflow" can start (step I). Specifically, for performing the coagulation test routine, the sample to be tested can be sucked-in from the corresponding sample vessel 33 in the sample storage area 36 and can be discharged into the reaction vessel 38 transferred to the incubation seat 11 by operating the first pipettor 23. Furthermore, one or more reagents related to the coagulation test can be sucked-in from the corresponding reagent containers in the reagent storage area 37 and can be discharged into the reaction vessel 38 by operating the second pipettor 24. According to one embodiment, at least one reagent can be pipetted using a heatable pipette of the second pipettor 24 so as to have an optimal reagent temperature for reacting with the sample. The reagents can be pipetted into the reaction vessel 38 prior to or after pipetting of the sample. Furthermore, pipetting may occur while gripped or while seated in a reaction vessel seat 6. In the incubation seat 11, sample and reagents contained in the reaction vessel 38 can be incubated (i.e., kept at a predefined temperature of, for example, approximately 37° C. for a pre-determined time interval) for the reaction to occur. Prior to or after incubation, the reaction vessel 38 can be lifted from the incubation seat 11 by the gripper 29 of the reaction vessel transferring device 16 and can be mixed by operating the mixing mechanism 42 and/or another reagent can be pipetted. The reaction vessel 38 can then be transported to one test seat 10 by the gripper 29, followed by an optical measurement of the turbidity of the sample using the coagulation test photometer 53.

Then, for continuing the "coagulation workflow", the reaction vessel 38 can be transported from the incubation block 8 to one reaction vessel seat 6 of the rotor 4 brought in the first picking position 17 by rotating the rotor 4 by operating the gripper 29 of the reaction vessel transferring device 16 (step J), followed by rotating the rotor 4 so as to bring the reaction vessel 38 into the second picking position 69 and removing the reaction vessel 38 from the rotor 4 by operating the gripper 29 of the input/output workstation 15 (step L). Specifically, in the second picking position 69, the reaction vessel 38 can be gripped by the gripper 29 of the input/output workstation 15 and can be transferred to the waste position 47. Then the "coagulation workflow" can end.

When sample testing with respect to clinical chemistry is ordered, for continuing the "clinical-chemistry workflow," a clinical-chemistry test routine embedded in the "clinical-chemistry workflow" can start (step K).

For performing the clinical-chemistry test routine, the sample to be tested by the various clinical-chemical tests can be sucked-in from the corresponding sample vessel 33 in the sample storage area 36 and can be discharged into one reaction vessel 38 on the rotor 4. Furthermore, one or more reagents related to the clinical-chemical tests can be sucked-in from the corresponding reagent containers in the reagent storage area 37 and can be discharged into the reaction vessel 38 on the rotor 4. The reagents can be pipetted into the reaction vessel 38 prior to or after pipetting of the sample. The reaction vessel 38 can then be transported to one first workstation 7 by rotating the rotor 4 for pipetting the sample and reagents. The reaction vessel 38 can then be gripped by the gripper 29 of the first workstation 7 and the mixing mechanism 42 can be operated. Then, the reaction vessel 38 can again be placed on a reaction vessel seat 6 of the rotor 4, followed by moving the reaction vessel 38 to the clinical-chemistry test photometer 52 for measuring the various clinical-chemical test parameters.

Then, continuing the "clinical-chemistry workflow", the reaction vessel 38 containing sample and reagents can be removed from the rotor 4 by rotating the rotor 4 to the second picking position 69 and operating the gripper 29 of the input/output workstation 15 (step L). Specifically, in the second picking position 69, the reaction vessel 38 can be gripped by the gripper 29 and can be transferred to the waste position 47. Then the "clinical-chemistry workflow" can end.

In one embodiment of the above-described workflows, the controller 28 can operate the first and second analytical units 2, 3 for at least temporarily simultaneously carrying out clinical-chemical tests on a plurality of samples contained in reaction vessels 38 of the rotor 4 and/or for at least temporarily simultaneously carrying out coagulation tests on a plurality of samples contained in reaction vessels 38 of the incubation block 8.

In one embodiment of the above-described workflows, sample tests can be ordered by user-interaction, for example, by typing-in corresponding instructions in a control panel. In one alternative embodiment, sample tests can be ordered by reading instructions stored in machine-readable information tags of sample racks 32 and/or samples vessels 33.

In a further workflow, the controller 28 can be setup to control a blank test for receiving an optical signal of an empty reaction vessel 38 for use with the first and/or second diagnostic tests in the rotor 4. Specifically, optical properties of empty reaction vessels 38 can readily be determined by operating the clinical-chemistry test photometer 52 so as to obtain a calibration signal to be used in coagulation tests and/or clinical-chemical tests of the samples.

In the above-described workflows, samples can be tested with respect to coagulation and clinical-chemical test parameters. Specifically, for performing the coagulation tests, reaction vessels 38 can be transported from the reaction vessel feeder 12 to the incubation block 8 via the rotor 4 wherein reaction vessels can be loaded onto the rotor 4 by the input/output workstation 15 and can be transported from the rotor 4 to the incubation block 8 by the reaction vessel transferring device 16. Furthermore, reaction vessels 38 can be transported from the incubation block 8 to the waste position 47 via the rotor 4 wherein reaction vessels can be loaded onto the rotor 4 by the reaction vessel transferring device 16 and transported from the rotor 4 to the waste position 47 by the input/output workstation 15. Furthermore, the rotor 4 can also be used for testing samples with respect to clinical-chemistry. Specifically, the rotational movement of the rotor 4 for moving empty reaction vessels 38 to the first picking position 17 and used reaction vessels 38 to the second picking position 69 can be synchronized with testing of samples with respect to clinical-chemistry.

A major advantage with respect to time and costs for processing samples can be given by the fact that the system 1 can have a variety of shared resources. Specifically, the sampling unit 26, the pipetting unit 22 and the reagent compartment 25 can be used for both coagulation and clinical-chemistry tests. Furthermore, the rotor 4 and the reaction vessel feeder 12 can be used for both testing samples with respect to clinical-chemical test parameters and transporting samples to/from the incubation station 8. Furthermore, by sharing components of the system 1 for both coagulation and clinical-chemical tests, the footprint of the system 1 can be greatly reduced compared to the case of providing individual system components. Moreover, reaction vessels 38 can be transported to the incubation block 8 in a highly time-efficient manner without a need to specify in advance for which tests individual reaction vessel 38 can be used.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A reaction vessel transferring device for an automated system for testing liquid samples, wherein the automated system comprises a first analytical unit for carrying out at least one first diagnostic test comprising a rotatable first vessel holder having a plurality of reaction vessel seats for detachably holding reaction vessels and a second analytical unit for carrying out at least one second diagnostic test comprising a stationary linear second vessel holder having a plurality of reaction vessel seats for detachably holding reaction vessels, the reaction vessel transferring device comprising:
   at least one gripper for gripping a reaction vessel and transferring reaction vessels from the first vessel holder to the second vessel holder and/or from the second vessel holder to the first vessel holder, wherein the reaction vessel transferring device is translatable parallel to the second vessel holder;
   a first part comprising a linearly translatable socket,
   wherein the gripper is attached to a gripper carrier, the gripper carrier is rotatably attached to the linearly translatable socket and has an attached guiding element which is brought in engagement with a guiding groove to control rotation of the gripper carrier with respect to the linearly translatable socket, and is configured to move at least in part along a curved path between a picking position and at least one reaction vessel seat of the second vessel holder by linear translation of the linearly translatable socket and by rotation of the gripper carrier with respect to the linearly translatable socket by the guiding element engaging the guiding groove as the linearly translatable socket moves linearly down a linear guiding rail.

2. The reaction vessel transferring device according to claim 1, further comprising,
   a resilient device for pre-tensioning the gripper carrier in rotation against the linearly translatable socket.

3. The reaction vessel transferring device according to claim 1, wherein the gripper is coupled to a mixing/shaking mechanism for mixing and/or shaking liquids contained in a gripped reaction vessel.

4. An automated system for testing liquid samples, the system comprising:
   a first analytical unit for carrying out at least one first diagnostic test comprising a rotatable first vessel holder having a plurality of reaction vessel seats for detachably holding reaction vessels;
   a second analytical unit for carrying out at least one second diagnostic test comprising a stationary linear second vessel holder having a plurality of reaction vessel seats for detachably holding reaction vessels; and
   a reaction vessel transferring device according to claim 1.

5. The automated system according to claim 4, further comprising,
   a pipetting unit comprising one or more pipettors for dispensing and/or withdrawing liquids into/from the reaction vessels;
   a reagent compartment for receiving reagent containers containing at least two types of reagents adapted to the first and second diagnostic tests;
   a sampling unit for receiving samples for the first and second diagnostic tests;
   at least one loading/unloading unit for loading and/or unloading reaction vessels on/from the first vessel holder; and
   a controller to operate the pipetting unit, the sampling unit and the at least one loading/unloading unit for carrying out the first and/or second diagnostic tests on the samples comprising operating the loading/unloading unit for loading reaction vessels on the first vessel holder and operating the reaction vessel transferring device for transferring reaction vessels from the first vessel holder to the second vessel holder and/or from the second vessel holder to the first vessel holder.

6. The automated system according to claim 5, wherein the controller controls a workflow, wherein the workflow comprises:
   operating the loading/unloading unit for loading one reaction vessel on the first vessel holder;
   operating the pipetting unit for dispensing one sample and one or more reagents adapted to the first diagnostic test into the reaction vessel;
   operating the first analytical unit for carrying out the first diagnostic test on the sample contained in the reaction vessel loaded on the first vessel holder; and
   operating the loading/unloading unit for unloading the reaction vessel from the first vessel holder.

7. The automated system according to claim 6, wherein the controller controls a workflow, wherein the workflow comprises,
   operating the loading/unloading unit for loading one reaction vessel on the first vessel holder;
   operating the reaction vessel transferring device for transferring the reaction vessel from the first vessel holder to the second vessel holder;
   operating the pipetting unit for dispensing one sample and one or more reagents adapted to the second diagnostic test into the reaction vessel;
   operating the second analytical unit for performing the second diagnostic test on the sample contained in the reaction vessel loaded on the second vessel holder;
   operating the reaction vessel transferring unit for transferring the reaction vessel from the second vessel holder to the first vessel holder; and
   operating the loading/unloading unit for unloading the reaction vessel from the first vessel holder.

8. The automated system according to claim 7, wherein the controller further,
   operates the first analytical unit for at least temporarily simultaneously carrying out one or more first diagnostic tests on samples contained in reaction vessels loaded on the first vessel holder;
   operates the second analytical unit for at least temporarily simultaneously carrying out one or more second diagnostic tests on samples contained in reaction vessels loaded on the second vessel holder; and
   operates the first and second analytical units for carrying out one or more second diagnostic tests on samples contained in reaction vessels loaded on the second vessel holder at least temporarily simultaneously with carrying out one or more first diagnostic tests on samples contained in reaction vessels loaded on the first vessel holder.

9. A method for transferring reaction vessels in an automated system for testing liquid samples, wherein the automated system comprises a first analytical unit for carrying out at least one first diagnostic test comprising a rotatable first vessel holder having a plurality of reaction vessel seats for detachably holding reaction vessels and a second analytical unit for carrying out at least one second diagnostic test comprising a stationary linear second vessel holder having a plurality of reaction vessel seats for detachably holding reaction vessels, the method comprising:

transferring reaction vessels from the first vessel holder to the second vessel holder and/or from the second vessel holder to the first vessel holder via a reaction vessel transfer device comprising a first part comprising a linearly translatable socket and a gripper carrier comprising a gripper rotatably attached to the linearly translatable socket and having an attached guiding element which can be brought in engagement with a guiding groove to control rotation of the second upper part with respect to the linearly translatable socket, wherein the transfer of reaction vessels comprises translating the linearly translatable socket parallel to the second vessel holder and moving the reaction vessels at least in part along a curved path between a picking position of the first vessel holder and at least one reaction vessel seat of the second vessel holder by linearly translating the linearly translatable socket and by rotating the gripper carrier with respect to the linearly translatable socket by the guiding element engaging the guiding groove as the linearly translatable socket moves linearly down a linear guiding rail.

10. The method according to claim 9, further comprising, transferring one reaction vessel from an incubation seat of the second vessel holder for incubating one sample and one or more reagents to one test seat of the second vessel holder for carrying out the second diagnostic test.

11. The method according to claim 10, wherein one sample and one or more reagents contained in one reaction vessel are mixed during transfer of the reaction vessel from one incubation seat to one test seat.

12. The method according to claim 9, further comprising, gripping the reaction vessel, wherein one sample and/or one or more reagents are pipetted into the gripped reaction vessel and/or wherein liquids are mixed in the gripped reaction vessel.

* * * * *